(12) United States Patent
Sevrain et al.

(10) Patent No.: US 8,491,870 B2
(45) Date of Patent: *Jul. 23, 2013

(54) METHOD FOR DETECTION AND TREATMENT OF ANEURYSMS

(75) Inventors: Lionel C. Sevrain, West Palm Beach, FL (US); Sylvie Y. Verdier-Sevrain, West Palm Beach, FL (US)

(73) Assignee: Lers Surgical, LLC, West Palm Beach, FL (US)

( * ) Notice: Subject to any disclaimer, the term of this patent is extended or adjusted under 35 U.S.C. 154(b) by 148 days.

This patent is subject to a terminal disclaimer.

(21) Appl. No.: 12/809,139

(22) PCT Filed: Nov. 23, 2008

(86) PCT No.: PCT/US2008/084445
§ 371 (c)(1),
(2), (4) Date: Jun. 28, 2010

(87) PCT Pub. No.: WO2009/085475
PCT Pub. Date: Jul. 9, 2009

(65) Prior Publication Data
US 2012/0164183 A1   Jun. 28, 2012

Related U.S. Application Data

(60) Provisional application No. 61/016,090, filed on Dec. 21, 2007.

(51) Int. Cl.
*A61K 49/00* (2006.01)

(52) U.S. Cl.
USPC .......................................................... 424/9.1

(58) Field of Classification Search
None
See application file for complete search history.

(56) References Cited

U.S. PATENT DOCUMENTS

| | | | |
|---|---|---|---|
| 5,057,313 A * | 10/1991 | Shih et al. | 424/1.53 |
| 6,387,622 B1 | 5/2002 | Siiman et al. | 435/6 |
| 2004/0043030 A1 * | 3/2004 | Griffiths et al. | 424/178.1 |
| 2005/0255484 A1 * | 11/2005 | Valkirs et al. | 435/6 |
| 2009/0017031 A1 * | 1/2009 | Fung | 424/139.1 |

FOREIGN PATENT DOCUMENTS

| WO | WO 87/05031 | 8/1987 |
|---|---|---|
| WO | WO 2007/092419 | 8/2007 |

OTHER PUBLICATIONS

Kassam et al. Altered arterial homeostasis and cerebral aneurysms: a review of the literature and justification for a search of molecular biomarkers. Neurosurgery. May 2004;54(5):1199-11; discussion 1211-2. Review.*
Cheuk et al. Differential expression of integrin alpha5beta1 in human abdominal aortic aneurysm and healthy aortic tissues and its significance in pathogenesis. J Surg Res. May 15, 2004;118(2):176-82.*
Low HL. Altered arterial homeostasis and cerebral aneurysms: a review of the literature and justification for a search of molecular biomarkers. Neurosurgery. May 2005;56(5):E1166.*
Sadamasa et al. Gene Expression during the Development of Experimentally Induced Cerebral Aneurysms. J Vasc Res 2008;45:343-349.*
Aoki et al Macrophage-derived matrix metalloproteinase-2 and -9 promote the progression of cerebral aneurysms in rats. Stroke. Jan. 2007;38(1):162-9.*
Miura et al. Cell Adhesion Molecule Expression in Coronary Artery Aneurysms in Acute Kawasaki Disease. Pediatr Infect. Dis J. 2004, 23:931-936.*
Wang et al. .Cartilage Oligomeric Matrix Protein Maintains the Contractile Phenotype of Vascular Smooth Muscle Cells by Interacting With alpha7beta1 Integrin. Circ Res. 2010;106:514-525.*
Zargham et al. alpha8beta1 Integrin expression in the rat carotid artery: involvement in smooth muscle cell migration and neointima formation. Cardiovasc Res. Mar. 1, 2005;65(4):813-22.*
Zargham R, Touyz RM, Thibault G. α8 integrin overexpression in de-differentiated vascular smooth muscle cells attenuates migratory activity and restores the characteristics of the differentiated phenotype. Atherosclerosis. 2007; 195: 303-312.*
Raines et al. Integrin α7β1 COMPels Smooth Muscle Cells to Maintain Their Quiescence. Circulation Research. 2010;106:427-429.*
Moiseeva. Adhesion receptors of vascular smooth muscle cells and their functions. Cardiovascular Research 52 (2001) 372-386.*
Yao et al. Functional expression of the alpha 7 integrin receptor in differentiated smooth muscle cells. Journal of Cell Science 110, 1477-1487 (1997).*
PCT International Preliminary Report on Patentability issued in International Application No. PCT/US2008/084445, mailed Jul. 1, 2010.
PCT International Search Report and Written Opinion issued in International Application No. PCT/US2008/084445, mailed Jun. 1, 2009.
Siiman et al., "Fluorescent neoglycoproteins: antibody-aminodextran-phycobiliprotein conjugates ," *Bioconjug Chem.*, 10(6):1090-1106, 1999.

* cited by examiner

*Primary Examiner* — Maher Haddad
(74) *Attorney, Agent, or Firm* — Novak Druce Connolly Bove + Quigg LLP

(57) ABSTRACT

The present invention generally concerns the detection and/or treatment of aneurysm in a non-invasive manner. In particular cases, the invention concerns methods and compositions for localizing a labeled composition to the site of an aneurysm for its detection and, in further cases, treatment of the aneurysm. In specific cases, the composition targets a subendothelial component of the aneurysmal wall, such as a smooth muscle cell exposed at the luminal surface of the vessel. In further specific cases, the composition targets an integrin receptor or laminin.

14 Claims, 2 Drawing Sheets

METHOD FOR DETECTION AND TREATMENT OF ANEURYSMS

The present invention is a national phase application filed under 35 USC §371 from PCT/US2008/084445, filed Nov. 23, 2008, which claims priority to U.S. Provisional Patent Application Ser. No. 61/016,090, filed Dec. 21, 2007, both of which applications are incorporated by reference herein in their entirety.

TECHNICAL FIELD

The present invention generally concerns at least the fields of medicine, cell biology, and molecular biology. In particular aspects, the present invention concerns the detection and/or treatment of cerebral aneurysms.

BACKGROUND OF THE INVENTION

Annually in the U.S., aneurysmal subarachnoid hemorrhage affects greater than 30,000 people. Ten to 15 percent of these individuals die before reaching the hospital and greater than 50 percent die within the first month following rupture. Of those patients that survive, approximately half suffer some permanent neurological deficit.

Intra-cranial saccular (berry) aneurysm is a balloon-like distension of a major brain artery occurring at (or near) the apex of arterial forks. It is frequently (90%) located on the anterior part of the circle of Willis. Various hypothesis have been proposed regarding the developmental mechanisms of Saccular Cerebral Artery Aneurysms (SCAAs) such as the medial defect theory (Forbus, 1930), the elastic lamellar theory (Glynn, 1940), degenerative theory (Stehbens, 1963; Stehbens, 1972), congenital theories (Bremer, 1943; Agnoli, 1982), and others (Sekha et al., 1981). Recently the development of an experimental animal model of the disease with pathological features very similar to those of human SCCA has made possible the study of the pathogenesis of human SCCAs (Hashimoto et al., 1978). It has been shown that hemodynamic stress induces the development of cerebral aneurysms causing degenerative changes of the endothelium, the elastic lamina and the medial smooth muscle cells at specific site on the arterial bifurcation (Kojima et al., 1988).

Histological Features of SCAAs

The anterior cerebral artery/olfactory artery (ACA/OA) junction is one of the most common sites of aneurysm development in the animal model. Its normal structure and changes due to aneurysm development have been widely studied.

1. Normal ACA/OA Artery Junction

The apex of a normal ACA/OA junction consists of normal arterial components (endothelial cells, internal elastic lamina, medial smooth muscle cells, and thin adventitial fibrous connective tissue). In the apical region, there is an intimal protrusion called pad consistently located near the apex on the distal side of the ACA. This pad is composed of spindle-shaped cells similar to the medial smooth muscle cells, rich in interstitial tissue. Under and just distal to the intimal pad on the side of the ACA, the internal elastic lamina is thinned and fragmented.

2. Aneurysm Formation at ACA/OA Artery Junction

The initial changes of aneurysm occur at the intimal pad and the neighboring distal portion. In the histological structure of early stage aneurysms, there are the following characteristics: 1) the wall does not significantly protrude; 2) initial changes are localized almost exclusively at the intimal pad and its neighboring distal portion; and 3) there is fragmentation of internal elastic lamina and slight thinning of the media (decrease of medial smooth muscle cells in number). In the histological structure of advanced stage aneurysms, there are the following characteristics: 1) aneurismal wall consists only of a fibrous adventitia and a layer of endothelial cells; 2) complete disappearance of the Internal Elastic Lamina (I.E.L) at the level of the aneurismal neck; and 3) media layer (smooth muscle cells (SMC)) ceases abruptly proximal to the neck.

The histological features of SCAAs include degenerative changes of endothelium, fragmentation and disappearance of I.E.L, and thinning (then disappearance) of medial layer. In degenerative changes of the endothelium, the following has been observed. Severe changes in endothelium have been reported. Nagata et al. (1981) examined by scanning electron microscopy the luminal surface of the cerebral aneurysms. They noticed some variations in the shape of the endothelial cells from fusiform to polygonal. Some of them showed balloon-like protrusions. Crater-like depressions on the endothelial surface and small holes and enlarged gaps at the junction of the endothelial cells were frequently observed. Gap formation at the junctions between the endothelial cells was one of the most obvious changes on the luminal surface of the aneurysms. Kojima et al. (1986) studying various stage of early aneurismal changes reported alterations of the endothelium developing just distal to intimal pad. Degenerated cells with balloons and craters were observed intermingled with regenerated endothelial cells. Interendothelial gaps were also seen. They concluded that some hemodynamic stress, possibly turbulent flow or secondary flow, may injure the endothelial cells located distal to the pad, and such injured endothelial cells in turn develop saccular cerebral aneurysms. Greenhill and Stehbens (1982) also described severe alterations of the endothelium and subendothelial tissues caused by hemodynamic stress. Kim et al. (1992) studied aneurismal changes in experimental monkeys and found endothelial injury. They suggested that aneurismal changes are initiated by degenerative changes in the endothelium, which are followed by alterations in the underlying elastic lamina and, in turn, in the medial layer.

Degenerative changes of the internal elastic lamina and the medial smooth muscle cells are also known. Hazama et al. (1986) showed that early aneurismal changes consist on degenerative changes of the Internal Elastic Lamina (I.E.L) at the intimal pad and the neighboring area distal to the pad associated to regressive changes of medial smooth muscle layer. Kim et al. (1988) also reported degenerative changes of the I.E.L and medial smooth muscle layer. Morimoto et al. (2002) found that the characteristic of SCAA formation in a mouse model was thinning of medial smooth muscle layer and disappearance of the I.E.L. Kondo et al. (1998) found that the histological features of aneurismal changes were thinning of the medial layer accompanied by fragmentation or disappearance of internal elastic lamina with wall dilatation. They noted a decreased number of SMCs in the medial layer due to apoptosis. They concluded that the death of medial SMCs through apoptosis plays an important role in aneurysm formation.

Molecular Mechanisms of SCAAs Formation

While the pathological features of aneurismal lesions described above are well documented, the precise molecular mechanisms involved in the formation of cerebral aneurysms have not yet been conclusively identified. Hemodynamic stress has been shown in many investigations to be the major cause of various degenerative changes in SCAA formation (Nakatani et al., 1991; Stehbens, 1989). This hemodynamic stress might induce a complex, multifactorial remodeling through a variety of mediators and pathways. Recent studies have reported the role of nitric oxide in the development of SCAA. Inducible NO synthase (iNOS) was induced in response to hemodynamic stress and NO synthesized by iNOS serves to damage the arterial wall and lead to aneurysm formation (Fukuda et al,. 2000). Other molecular mechanisms such as active expressions of matrix metalloproteinases (Houghton et al., 2006), apoptosis of medial smooth muscle cells (Cohen et al., 1991) have been shown associated with SCAA. The role of elastase in the degradation of I.E.L in early aneurismal lesions has also been discussed. Nagata et al. (1981) reported that in experimental aneurysms many leukocytes were present adhering to the inter endothelial gaps, which may represent the participation of leukocytes in degradation of the I.E.L. Cajander and Hassler (1976) also found extracellular lysosome-like granules closely connected to the disintegrated elastic lamella in the mouths of aneurysms and hypothesized that discharged leukocyte granules containing elastase help to destroy the elastic lamella. Enhanced activity of elastase in the arterial wall may also participate in the degenerative changes of the internal elastic lamina, as in the case of hypertension (Yamada et al., 1983).

Two studies have brought significant insights into the mechanism of formation of cerebral aneurysms.

1. Futami et al. (1995) have demonstrated that fibronectin (as well as collagen IV and I) normally expressed in the subendothelium of artery, disappears in early aneurysmal lesions. The absence of fibronectin in the aneurysm wall is a critical feature in aneurysm formation considering the role of this Extra-cellular Matrix (ECM) protein in wound repair and its role in modulation of SMC phenotype (see below).

2. Jamous et al. (2007) have demonstrated the sequence of ultrastructural, morphological and pathological changes leading to the formation of saccular intracranial aneurysms in vivo. They used the current established animal model to induce cerebral aneurysm. They studied the anterior cerebral artery-olfactory artery bifurcation morphologically by using vascular corrosion casts and immunohistochemically by using specific antibodies against endothelial nitric oxide synthase (eNOS), α-smooth muscle actin (α-SMA: marker of SMCs), macrophages, and matrix metalloproteinase-9. They showed that the formation of intracranial aneurysms starts with endothelial injury at the apical intimal pad (evidenced by the loss of eNOS expression) (stage I); this leads to the formation of an inflammatory zone. This inflammatory zone shows subendothelial expression of α-SMA and a loss of eNOS. There is no protusion on the vessel wall at this early inflammatory stage (stage IIA). The progression of inflammation results in arterial wall destruction and the development of a defect presenting as a narrow slit; this is associated with protusion of the vessel wall (Stage IIB). This defect is continuous with the lumen of the parent artery, lacks eNOS expression, and contained α-SMA positive SMCs and macrophages. Expansion of this defect results in the formation of a saccular dilatation (stage III). The walls of the cavity continued to lack eNOS expression, contained a layer of α-SMA-positive SMCs and are positive for MMP-9 expression. The authors suggested that endothelial injury and exposure of the subendothelial matrix initiate platelet activation and adhesion. Activated platelets secrete growth factors that contribute to the recruitment of macrophages and promote migration of SMCs. These processes result in the formation of the inflammatory zone. The combined effects of hemodynamic changes and the destructive effects of macrophages through their release of proteolytic enzymes may lead to development of the defect.

Scanning electron microscopy studies of vascular corrosion casts of the ACA-OA bifurcation and double immunostaining of the vascular wall illustrates that normal endothelial cells are seen at the apical intimal pad, and the endothelial cell markings are elongated in the direction of the blood flow. The endothelial and the smooth-muscle layer form two continuous layers. In stage I, there are roughened apical intimal pad with irregularly shaped imprints, and loss of eNOS expression at the apical intimal pad is observed. In stage IIA, there is shallow elevation surrounded by an area of depression of the apical intimal pad. Swelling of the vessel wall at the apical intimal pad is shown, and part of this swollen area lacks eNOS expression and shows subendothelial expression of α-SMA-positive cells. In stage IIB, there is pyramid-shaped elevation of the apical intimal pad, and the surface of this elevation is covered by abnormal imprints. Thinning and degradation of the smooth-muscle layer creates a defect in the inflammatory zone (arrow) and produces vessel wall protrusion. In stage III, there is saccular aneurysm covered with abnormal imprints, expansion of the inflammatory zone defect, and destruction and protrusion of the vessel wall representing the nidus of the cerebral aneurysm.

Stage IIA has early inflammatory changes characterized by SMC migration and macrophage infiltration. A sagittal cut of the left ACA-OA bifurcation viewed at low and high magnification shows swelling of the apical intimal pad. Double immunostaining of an ACA-OA section with eNOS antibodies and α-SMA shows swelling of the vessel wall at the apical intimal pad; part of this swollen area lacks eNOS expression and shows migration of a-SMA-positive cells into the neointima. In triple immunostaining of an ACA-OA section with antibodies against eNOS, α-SMA, and macrophages, macrophage expression confirms the presence of an inflammatory zone.

BRIEF SUMMARY OF THE INVENTION

The present invention generally concerns a method for detection of aneurysms, including cerebral aneurysm, using non-invasive molecular imaging techniques, and in particular cases further concerns treatment of the aneurysm.

The present invention can detect any aneurysm, regardless of the stage or type of the aneurysm. In early stage aneurysms, the initial changes are characterized by the alteration of the endothelium and subendothelium and migration of medial smooth cells in the intima. At the late stage of degeneration, there is a disappearance of the media, and the aneurysmal wall just consists in an endothelium and a few fibers of collagen (adventicia). However, because these different stages of degeneration coexist in the same aneurysm, the invention can detect any aneurysm.

In particular aspects of the invention, the methods and compositions concern targeting a specific component of the subendothelium at the aneurysm. In certain cases, the specific component in the subendothelium that is targeted by compositions of the invention for the detection of aneurysmal lesions are migrating SMCs that are in a contractile phenotype, which is in contrast to SMCs in neointima formation that are in a synthetic phenotype. That is, specific markers of SMC phenotype will allow one to differentiate SMCs in aneurysmal wall from SMCs in neointima. In specific embodiments, particular proteins on the surface of SMCs unique to contractile SMCs are the targets for detection/treatment of the aneurysm. In specific embodiments, integrin receptors can serve as markers of SMC phenotype. In further specific embodiments, the differentiated contractile SMCs comprise α1β1 integrin (which is a receptor for laminin, collagen I, and collagen IV) and α7β1 integrin, which is a receptor for laminin-1. However, in the arterial wall, α1β1 integrin is expressed on SMCs but also on macrophages (which invade the arterial wall in pathological conditions such as atherosclerosis and aneurysm). Therefore, in some embodiments α7β1 is targeted, because in the arterial wall it is expressed exclusively by SMCs. α7 integrin expression confers a gain of function-motile phenotype to immobile cells and is responsible for transduction of the laminin-induced cell motility, in certain aspects of the invention. Laminin-1 is also useful in the invention as a marker of aneurysmal lesion, because it is the specific ligand of α7 integrin, and α7 integrin mediates adhesion and migration of SMCs on laminin-1.

Thus, methods of the present invention are based at least in part on two characteristic features of early aneurysmal lesions: 1) the degeneration of endothelium and subendothelium that exposes underlying components; and 2) the migration in the subendothelium of SMCs of contractile, migrating phenotype (α7 integrin positive cells that bind specifically laminin-1). In specific cases, the method employs a labeled antibody directed against α7 integrin or laminin-1, for example, and the labeled antibody will have such characteristics that it binds exclusively to SMCs exposed at the luminal surface of the vessel, as opposed to being within the media. That is, such labeled antibody will not be able to bind contractile SMCs in the medial layer of normal arterial wall. In particular cases, the labeled antibody is coupled to a macromolecular compound (such as Dextran, for example) that keeps the compound in the intravascular compartment but yet allows it to be cleared from the intravascular compartment. Such a compound will bind exclusively SMCs exposed at the luminal surface of the vessel due to endothelial and subendothelial degeneration but will not be able to bind contractile SMCs in the medial layer of normal arterial wall. In vivo detection of the aneurysm is achieved, and the method may use different molecular imaging techniques such as immunoscintigraphy using antibody radiolabeled with 99mTc-dextran or MRI using antibody conjugated to Gadolinium-DTPA-dextran, for example.

In one embodiment of the invention, there is an isolated composition, comprising a cell targeting molecule, an intravascular targeting molecule, and a label. In a specific embodiment, the composition further comprises a therapeutic agent. In a further specific embodiment, the cell targeting molecule is an antibody or a peptide. In specific embodiments, the antibody immunologically reacts with an integrin receptor on the cell surface of smooth muscle cells or a laminin (such as laminin 1). In certain aspects, the integrin receptor is α1β1, α7β1, α3β1, or α8β1. In particular embodiments, the intravascular targeting molecule is a polymer, such as one selected from the group consisting of dextran, albumin, transferrin, globulins, pectin, gelatin, and cellulose derivatives. In some cases, the label is a radionuclide, a fluorophore, a lucigen, or a paramagnetic chelator or microbubble contrast agent. In further embodiments, the therapeutic agent is selected from the group consisting of a thrombogenic molecule, a polymerisable molecule, fibrinogen, a cell matrix protein (such as elastin, fibronectin, or laminin), a synthetic peptide, a cell growth factor, an elastase inhibitor, and a MMP inhibitor. In particular cases, the composition is comprised in a pharmaceutically acceptable excipient.

In another embodiment of the invention, there is a method of detecting and/or treating a cerebral aneurysm in an individual, comprising the step of delivering an effective amount of a compound of the invention to the individual. The individual may be at risk for developing an aneurysm, has a history of cerebral aneurysm, or is asymptomatic with no history or known risk of cerebral aneurysm (method may be used as a mass detection or routine screen for individuals). In specific cases, the composition is delivered to the individual once or more than once. In certain aspects, the individual is provided an additional therapy for aneurysm, such as one that comprises medication, surgery, endovascular coiling, or a combination thereof.

In another embodiment of the invention, there is a kit for detection and/or treatment of aneurysm, comprising the compound of the invention, housed in a suitable container. In specific embodiments, the kit further comprises a therapeutic agent.

In general embodiments of the invention, one may be able to differentiate individuals in an "at-risk" aneurysm subgroup within a cerebral aneurysm population.

In particular aspects of the invention, α1β1, α7β1, α3β1, α8β1 integrins, and/or laminin 1 are indicators that there is a risk for an aneurysm to rupture; in specific embodiments, one can utilize one or more of these targets to detect the cerebral aneurysms, that are prone to rupture.

In other specific embodiments, the α7 expression, or the ratio of expression of α7/α5 is a marker of aneurysm that is "at risk" of rupture.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

Figure 1:
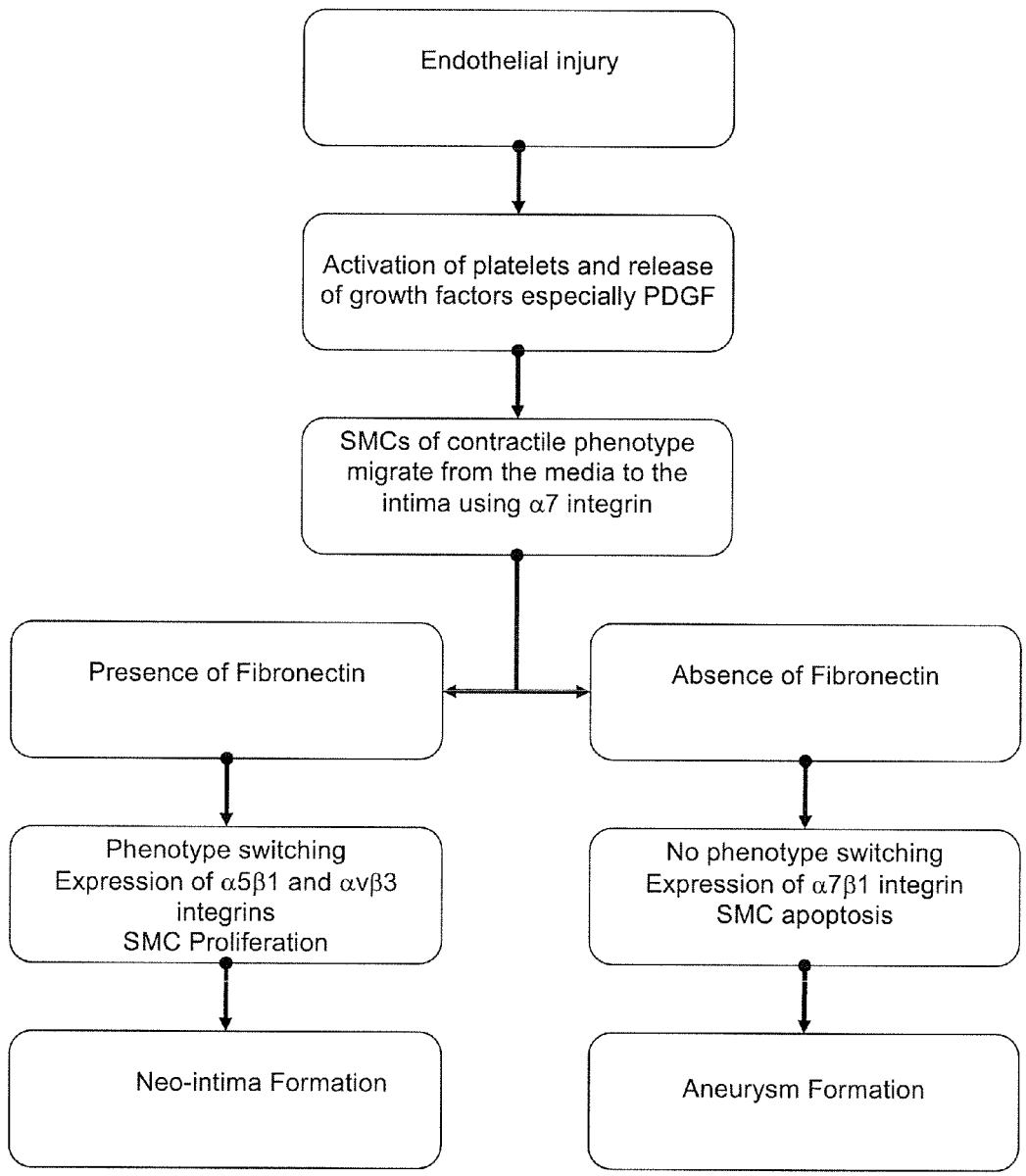
FIG. 1 is an exemplary schema outlining embodiments of the present invention for cerebral aneurysm formation versus neointima formation.

This application incorporates WO 2007/092419 by reference herein in its entirety.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

I. Definitions

The term "aneurysm" as used herein refers to an abnormal bulge or "ballooning" in the wall of an artery.

The term "cerebral aneurysm" as used herein refers to a cerebrovascular disorder wherein a localized weakness in the wall of a cerebral blood vessel (artery) results in a localized dilation or ballooning of the blood vessel. The majority of aneurysms are saccular in shape. It may also be referred to as a Saccular Cerebral Arterial Aneurysm (SCAA) or intracranial aneurysm.

The term "effective amount" or "therapeutically effective amount" as used herein is defined as an amount of the agent that will decrease, reduce, inhibit or otherwise abrogate an aneurysm. Thus, an effective amount is an amount sufficient to detectably and repeatedly ameliorate, reduce, minimize or limit the extent of the disease or at least one of its symptoms.

As used herein, the term "tunica intima" (or just intima) comprises a layer of endothelial cells supported by a basement membrane and an internal elastic lamina. The connective tissue between the endothelium and the internal elastic lamina is called "subendothelium." The internal elastic lamina (I.E.L) is part of the intima.

As used herein, the "subendothelium" is a definite zone within the intima and corresponds to the connective tissue between endothelial cell layer and inner elastic lamina.

As used herein, the "tunica media" refers to the main layer of the artery wall and comprises SMCs.

The "tunica adventitia" as used herein refers to the outermost layer and comprises mostly collagen. Cerebral arteries do not have the external elastic lamina unlike systemic arteries.

II. General Embodiments of the Invention

Intracranial aneurysms are a major public health problem; it is estimated that approximately 5% of the population harbors an unruptured intracranial aneurysm (Iwamoto et al., 1999). The consequences of rupture are catastrophic: approximately 50% of patients die during the first post-rupture month, and 60% of deaths occur within 2 days of the onset of aneurismal sub-arachnoid hemorrhage (SAH) (Broderick et al., 1994). Half of the survivors manifest physical or psychosocial deficits 1 year after SAH (Hackett and Anderson, 2000). Clip placement and coil occlusion to treat ruptured intracranial aneurysms, aimed at avoiding recurrent bleeding, have no direct effect on the recovery from the initial hemorrhage.

For surgical clipping, after a craniotomy, the surgeon then spreads the brain tissue apart, opens the subarachnoid cisterns under operative microscope and then places a tiny metal clip across the neck to stop blood flow into the aneurysm and exclude it from the blood stream. Endovascular treatment of brain aneurysms is a minimally invasive procedure which requires insertion of a catheter into the femoral artery and navigating it through the vascular system into the aneurysm (referred to as Endovascular Coiling (Guglielmi detachable coil)). Tiny platinum coils are threaded through the catheter and deployed into the aneurysm, blocking blood flow into the aneurysm and preventing rupture. However, these treatments are responsible for 15% of the morbidity and mortality. Recurrence is not insignificant: 2.2% at 10 years and 9.0% at 20 years (Molyneux et al., 2002). Given the poor prognosis of ruptured intracranial aneurysms, cerebral aneurysms should be detected before rupture, however current diagnosis means are invasive and expensive (e.g., 4-axle digital subtraction angiography), and no mass detection can be currently considered. Therefore, there is a need for developing non-invasive diagnosis and safer treatment for intracranial aneurysms.

Preliminary data from the literature have suggested that degeneration of the endothelium and subendothelium at specific site on the bifurcation of cerebral arteries is a characteristic feature of cerebral aneurysm formation. In the present invention, these degenerative changes render underlying components of the arterial wall abnormally expressed at the luminal surface of the artery, and these components are a useful a target for in vivo intravascular immuno-detection of cerebral aneurysms. The diagnosis of aneurismal lesions is made by coupling a specific antibody directed against a subendothelial component of the arterial wall to a label moiety, in certain cases. In specific embodiments, the labeled antibody is coupled to a compound (such as dextran) that confines it into the intravascular compartment, yet allows it to be rapidly cleared from the intravascular space. This method allows the diagnosis of cerebral aneurysm at an early stage, rendering possible a biological treatment for repairing the wall before irreversible damages. The treatment uses the same specific antibody coupled to a therapeutic moiety. Several therapeutic agents have already been considered such as the use of a thrombogenic or polymerisable molecule (intended to clog the aneurysms) or proteins (elastin, fibronectin, or fibrinogen, for example), or cell growth factors (intended to reinforce or make the fundus thicker and stronger). Thus, an antigenic component of the subendothelium of the arterial wall is useful for in vivo immuno-detection of early-stage aneurysm, although any stage of aneurysm may be detected and treated with the present invention.

III. Cerebral Aneurysm

The present invention is useful for detection and treatment of any cerebral aneurysm. Cerebral aneurysms are classified by size and shape, with small aneurysms having a diameter of less than 15 mm and larger aneurysms are those classified as large (15 to 25 mm), giant (25 to 50 mm), and super giant (over 50 mm). Saccular aneurysms, the most common form, have a saccular outpouching, whereas berry aneurysms are particular saccular aneurysms having necks or stems resembling a berry. Fusiform aneurysms lack stems.

Cerebral aneurysms commonly occur on the arteries at the base of the brain, known as the Circle of Willis. About 85% of cerebral aneurysms develop in the anterior part of the Circle of Willis, thereby involving the internal carotid arteries and their major branches that supply the anterior and middle sections of the brain. Common locations are as follows: the anterior communicating artery (30-35%), the bifurcation of the internal carotid and posterior communicating artery (30-35%), the bifurcation of the middle cerebral artery (20%), the bifurcation of the basilar artery, and the remaining posterior circulation arteries (5%).

Cerebral aneurysms may occur at any age, although they are more common in adults than children, and more common in women than men.

Most of intracranial aneurysms are clinically quiescent until they rupture. Onset of the aneurysm usually is sudden, with no warning. Rupture of a cerebral aneurysm often results in bleeding into the subarachnoid space or the brain itself, resulting in a subarachnoid hemorrhage (SAH) or intracranial hematoma (ICH) (Ruptured aneurysm). Although unruptured aneurysms are usually asymptomatic, some may be known either because they are multiple (The 4-axle digital subtraction angiography may reveal multiple unruptured aneurysms), or symptomatic (third cranial nerve palsy, headache, orbital pain) or incidental (brain imaging performed for a neurological non-aneurysmal disease)

The histology of normal cerebral artery junction is described as follows: the intimal pad is just distal to apex on distal side of ACA, and the pad is composed of spindle-shaped cells similar to the medial smooth muscle cells; the internal elastic lamina is continuous along the curvature of the apex, but at the proximal margin of the intimal pad, it is split into several layers and considerably fragmented under the intimal pad, and just distal to the intimal pad, it is thinned and fragmented for a short distance; no medial defect is found. In early stage aneurysms, initial changes are localized almost exclusively at the intimal pad and its neighboring distal portion; the wall does not significantly protrude; and there is fragmentation of internal elastic lamina and slight thinning of the smooth muscles cells layer. In advanced stage aneurysms, there is complete disappearance of the internal elastic lamina at the level of the aneurysmal neck, the media layer (SMC) ceases abruptly proximal to the neck, and the aneurysmal wall consists only of a fibrous adventitia and a layer of endothelial cells. Aneurysms form when hemodynamic stress plus pulsatile flow patterns initiate degenerative changes in the endothelial layer adjacent to the apex (distal side) of the arterial bifurcation, and these endothelial injuries are followed by degenerative changes in the internal elastic lamina, then in the medial layer (affecting the SMCs).

IV. Risk Factors for Rupture of Aneurysm

After an aneurysmal subarachnoid hemorrhage, nearly half of the patients die, with the remaining half who survive suffering from irreversible cerebral damage. More unruptured cerebral aneurysms are identified with increasing use of non-invasive neuro-imaging techniques (for example, magnetic resonance and computerized tomography angiography). The risk of rupture in aneurysms smaller than 10 mm is a 0.5 to 2% annual risk, in specific embodiments. Growing aneurysms and those larger than 10 mm run a higher risk for rate of rupture.

Risk factors for aneurysm rupture include the size of aneurysms in stable compared With Growing Lesions. In the ISUIA (ISUIA=International Study of Unruptured Intracranial Aneurysms) (1998) it has been pointed out that the size and location of aneurysms were independent predictors of rupture. In Group 1, aneurysms that were 25 mm or more in diameter had a rupture rate of 6% in the 1st year. It was observed that aneurysms that ruptured at a later time had more often increased significantly in size (> or =1 mm) than the largest aneurysms in patients without bleeding (Juvela, 1993, 2002, and 2000).

Locations of aneurysms may also be a factor. For example, aneurysms of the vertebrobasilar and middle cerebral arteries have a statistically higher probability of subsequent bleeding. In ISUIA Group 1, for example, the relative risk of rupture was 13.8 for aneurysms that were located at the basilar tip, whereas the relative risk was 13.6 for those in the vertebrobasilar or posterior cerebral artery distribution, compared to other locations. For posterior communicating artery aneurysms, the relative risk of rupture was 8.0. The relative risk of rupture was 5.1 for aneurysms at the basilar tip in Group 2.

The shape of the aneurysms has an impact on rupture, in specific examples. For example, multilobed lesions have a significantly higher risk of hemorrhage than do single-lobed unruptured aneurysms. In some embodiments, the age and sex of the individual is a factor; females have a risk factor affecting both aneurysm formation and growth, for example. In other cases, cigarette smoking hastens the growth of pre-existing aneurysms (Juvela, 2002).

Families having intracranial aneurysms and rupture history have a greater risk for rupture. In families with two or more first-degree members, especially siblings and mother-daughter pairs, or two first- and second-degree members with SAH, the risk that other relatives will harbor unruptured intracranial aneurysms is approximately 9 to 11%, which is higher than in the general population (Raaymakers et al., 1998; Ronkainen et al., 1997)

Finally, genetic conditions in some cases have an impact on risk factors for aneurysm rupture. For example, the presence of ADPKD (ADPKD=autosomal-dominant polycystic kidney disease) is associated with a 15% prevalence (Rinkel et al,. 1998) of cerebral aneurysms. Individuals having Type IV Ehlers-Danlos syndrome, hereditary hemorrhagic telangiectasia, neurofibromatosis Type 1, alpha-1-antitrypsin deficiency, Klinefelter syndrome, tuberous sclerosis, Noonan syndrome, or alpha-glucosidase deficiency have a propensity for intracranial aneurysms compared with the general population, in certain embodiments of the invention.

V. Exemplary Molecular Basis of the Invention

Due to the degeneration of the endothelium and subendothelium of the aneurysmal wall, SMCs that migrate into the intima are abnormally exposed at the luminal surface of the arterial wall and become available to react with labeled antibodies. These cells can be labeled in vivo using a cell surface marker (cytoskeletal antigen (such as $\alpha$-SMA) are protected from extracellular fluid by the cellular membrane and can not be labeled in vivo).

The present invention exploits the pathogenesis of cerebral aneurysm in which smooth muscle cells (SMCs) have a critical role. Therein, one or more cell surface markers of SMCs, for example specific integrin receptors, are antigenic components in the arterial wall targeted for in vivo immuno-detection of aneurysm.

A. Background on Smooth Muscle Cells (SMCs) and Their Role in Arterial Wall Repair After Injury 1. Smooth Muscle Cell (SMC)

SMC is the sole cell type normally found in the media of mammalian arteries. In the adult, it is a terminally differentiated cell that expresses cytoskeletal marker proteins like smooth muscle alpha-actin ($\alpha$-SM actin) and smooth muscle myosin heavy chain (SMMHC), and contracts in response to chemical and mechanical stimuli. They take part in the control of blood pressure and flow; at this stage they are referred to as being in a contractile phenotype. However, the smooth muscle cell is able to revert to a proliferative and secretory active state equivalent to that seen during vasculogenesis in the fetus; at this stage they are referred to as being in a synthetic phenotype. SMCs in their synthetic phenotype have a fibroblast-like appearance, a prominent endoplasmic reticulum and Golgi complex, few filaments and only a weak reactivity for $\alpha$-SM actin. They secrete extracellular matrix components: laminin, fibronectin, collagen and elastin (Thyberg et al,. 1997; Hultgardh-Nilsson et al., 1997). The transition from a contractile to a synthetic phenotype occurs in vascular diseases such as atherosclerosis and restenosis after angioplasty. In these diseases, in response to endothelial injury, smooth muscle cells migrate from the media to the intima, they dedifferentiate into a synthetic phenotype, proliferate and secrete components of the extracellular matrix and form what is called a neointima or myo-intimal hyperplasia or intimal thickening (Campbell and Campbell, 1985; Schwartz and Reidy, 1987). Neointima formation is a common mechanism of arterial wall repair after endothelial injury 2. Factors that Control SMC Phenotype Thyberg et al. (1997) have made extensive research on the control of SMC phenotype. They demonstrated first that laminin promotes the expression of a differentiated smooth muscle phenotype in vitro and in vivo, whereas fibronectin stimulates the cells to adopt a synthetic phenotype. Then, they demonstrated that after being converted into a synthetic phenotype, the cells do not start to proliferate without exogenous mitogen stimulation. They showed that some growth factors and especially platelet-derived growth factor (PDGF) stimulates SMC proliferation. After stimulation with PDGF, converted SMCs divide and produce their own PDGF which stimulates their growth in an autocrine and paracrine manner (Sjolund et al., 1988). Therefore, it is concluded that at least two requirements need to be fulfilled for inducing the synthetic, proliferating phenotype of SMCs:

First, the cells must adhere to a substrate of fibronectin and second, they must be stimulated with growth factors and especially PDGF. These studies are in agreement with others demonstrating that there is an accumulation of fibronectin at the site of arterial injury, in association with neointima formation (Bauters et al,. 1995; Chemnitz and Collatz Christensen, 1983) suggesting an important pathophysiological role of fibronectin in neointima formation and vascular wall repair (Hedin and Johan, 1987; Boudreau et al., 1991; Molossi et al., 1995). To modulate the phenotype of SMCs, laminin and fibronectin bind to integrin receptors on the surface of SMCs.

3. Integrin Receptors on SMCs

Integrins are a family of receptors involved in cell interactions with extracellular matrix (ECM) components and with other cells. Each integrin receptor is a heterodimer in which one of several homologous α subunits associates noncovalently with a β subunit. Some integrin subunit combinations recognize multiple ligands, while others are relatively specific. Although some integrins are widely expressed by a variety of cell types, others have a restricted distribution.

a. Integrin Receptors for Laminin

Several integrins (α1β1, α2β1, α3β1, α6β1, α7β1 and αvβ3) bind laminin (Clyman et al,. 1994). It has been demonstrated that only α1β1, α3β1, α7β1 and αvβ3 are expressed on human SMCs in vivo. α2β1 is a receptor for collagen I to VI and laminin. Despite the potentially significant in vitro functions of α2β1 in modulating SMC behavior, studies were unable to detect this integrin complex in normal or atherosclerotic human arteries (Glukhova et al., 1993). α6β1 has not been detected in SMCs in vivo (Thorsteinsdottir et al., 1995).

α1β1: is a receptor for laminin, collagen-I, collagen IV. Human medial SMCs (which in vivo are surrounded by a basement membrane that contains laminin-1 and/or laminin 3 and collagen IV) express high level of α1β1. α1 subunit expression is an exceptional feature of SMCs. Other cell types (fibroblasts, endothelial cells, keratinocytes, striated muscles, and platelets) contained trace amounts of α1β1 integrin (Belkin et al., 1990). Only activated T cells, monocytes also express α1β1 integrin. α1β1 integrin expression is characteristic of differentiated SMCs. It has been demonstrated that SMCs from intimal thickening of human adult aorta express less α1 subunit of α1β1 integrin than SMCs from adult aortic media (Belkin et al,. 1990). In contrast, it has been reported in a rat vascular injury model that α1β1 is expressed by intimal SMC in response to vascular injury (46). This discrepancy may be explained by the species-specificity of integrins.

α3β1: is able to bind a variety of ECM components including laminin, nidogen/entactin, fibronectin, and collagen I. It is expressed in vivo in medial SMC of human artery (Hillis et al., 1998). It is also expressed on B-lymphocytes and cells of kidney glomerulus.

α7β1: is a specific receptor for laminin-1. This integrin has a highly tissue-specific and limited expression pattern. It is a muscle specific integrin being expressed by all major types of muscle tissue, including skeletal, cardiac and smooth muscle. Its presence in all muscle types suggests a role for this integrin in transducing myofilament-generated forces to anchoring sites in the surrounding laminin-rich basement membrane during cellular contractile activity. No studies have documented the expression of α7β1 in human vascular SMCs. But, it has been demonstrated that murine vascular SMCs express the α7 integrin receptor. The expression of α7 integrin in SMCs is associated with their differentiated phenotype and mediates their interaction with laminin (Yao et al., 1997). Studies have demonstrated that α7 integrin expression confers a gain of function-motile phenotype to immobile cells and may be responsible for transduction of the laminin-induced cell motility (Echtermeyer et al., 1996). Therefore, in embodiments of the invention, there is a role of α7 integrin in migration of SMCs to the intima after vascular injury. It is likely that during neointima formation, highly differentiated SMCs, which were originally arranged in concentric layers and encircled by basement membranes, become motile and migrate into the intima toward growth factor signals using laminin-binding α7 integrin. In the intima, growth factors (especially PDGF) and extracellular matrix (fibronectin) modulate SMC phenotype and integrin expression (switching from α7 to α5β1 integrin expression) leading to the formation of a neointima. Furthermore, a recent study has demonstrated the importance of α7 integrin in vascular remodeling (Welser et al., 2007). Using a carotid ligation animal model, the authors have found a profound increase in vascular remodeling and neointima formation in the carotid arteries of α7 integrin-null mice subjected to ligation.

αvβ3: is able to bind a variety of ECM components including laminin, vitronectin, von Willebrand factor, thrombospondin, osteopontin, fibrinogen and fibronectin. It is expressed on different cell types including platelets, endothelial cells and SMCs. Studies have demonstrated that αvβ3 is expressed on SMCs in the media of normal as well as atherosclerotic coronary artery and on SMCs in the neointima. αvβ3 was also strongly expressed by luminal endothelium (Hoshiga et al,. 1995). Clinical studies have shown that c7E3, an antibody directed against β3 integrin reduces SMC migration and neointima formation and is useful in the prevention of the SMC response in restenosis after angioplasty (Topol et al., 1997).

b. Integrin Receptors for Fibronectin

The integrin receptors for fibronectin are α3β1, α4β1, α5β1, α8β1, αv β1, αv β3, α-IIb/β. α4β1, α5β1, α8β1, αv β1 are specific receptor for fibronectin (Topol et al., 1997).

α5β1: is a specific receptor for fibronectin. This integrin has been found to be expressed by SMCs in the media of human aorta whereas this protein was absent in the destructive media of aneurysmal aorta. The marked decrease in integrin α5β1 correlated to a decrease in density of SMCs (Cheuk and Cheng, 2004). Studies in a rat model of vascular injury, have shown that α5β1 integrin was not expressed in medial SMCs but highly expressed after vascular injury by the less differentiated SMCs at the luminal surface of the neointima.

This subpopulation of α5β1 positive SMCs repairs the arterial wall by assembling the fibronectin matrix. Soluble fibronectin protomers polymerize on the surface of these α5β1 positive cells. This assembly process is of paramount importance for wall repair because only insoluble fibrillar fibronectin can act as an adhesive ligand and regulate cell function (Pickering et al., 2000). In conclusion, these data indicate that α5β1 integrin, a specific receptor for fibronectin is critical for maintaining the integrity of the medial layer of normal artery and for the processus of wall repair and neointima formation after vascular injury. It is also expressed by T cells, monocytes, platelets.

α8β1: is a specific receptor for fibronectin. α8 subunit has a restricted cellular distribution. It is expressed in vascular and visceral smooth muscle cells. SMCs of arteries show an intense staining. The endothelial cells of vessels do not stain. The cells that expressed α8 subunit function as contractile cells (Schnapp et al., 1995).

c. Integrin Receptors as Markers of Smooth Muscle Cell Phenotype

According to the above data, α1β1, α7β1, α3β1, α8β1 are useful specific markers of differentiated contractile SMCs (these integrins are highly specific of SMCs and are not expressed by other cell types such as endothelial cells or platelets). Moreover, α7 integrin-expression confers a gain of function-motile phenotype to immobile cells and may be responsible for transduction of the laminin-induced cell motility.

In contrast, α5β1 a specific receptor or fibronectin is expressed by less differentiated SMCs of the neointima formation and is critical for fibronectin assembly and wall repair after injury. αvβ3 is an integrin that is widely expressed in the vessel wall (endothelial and SMCs cells) and has multiple ECM ligands is overexpressed in neointima formation.

d. Neointima Formation in Occlusive Arterial Disease

Neointima formation is a common mechanism of arterial wall repair after endothelial injury and occurs in vascular diseases such as atherosclerosis and restenosis after angioplasty. Endothelium injury induces platelet adhesion which induces the release of growth factors and especially PDGF. PDGF stimulates migration of SMCs for the media to the intima. Within the intima, SMCs bind fibronectin (FN) of the basement membrane. Fibronectin stimulates the cells to adopt a synthetic phenotype and then PDGF stimulate the proliferation of the dedifferentiate SMCs. SMCs in the neointima highly expressed α5β1 and αvβ3 integrins.

B. Exemplary Model for Pathogenesis of Cerebral Aneurysm

It has been demonstrated that hemodynamic stress is responsible for endothelium injury. But, in contrast to vascular diseases such as atherosclerosis and restenosis after angioplasty, neointima formation does not occur and there is no repair of the arterial wall. During aneurysm formation, there is disappearance of the medial layer. At an advanced stage, the aneurysm wall consists only of a fibrous adventitia and a layer of endothelial cells. Therefore, some factors that contribute to wound healing may be missing in the course of cerebral aneurysm formation. As described above, studies have demonstrated that fibronectin (as well as collagen IV and I) normally expressed in the subendothelium of artery, disappears in early aneurysmal lesions. This degeneration of the endothelial basement membrane and the subendothelial connective tissue may be due to endothelial dysfunction. Indeed, degeneration of endothelial cells in aneurismal walls has been demonstrated by scanning electron microscopy (described above) and these degenerated cells may decrease the production of ECM. Also, hemodynamic stress by itself may alter the subendothelium matrix. The absence of fibronectin in aneurysm wall is a critical feature in aneurysm formation considering the role of this ECM protein in wound repair and its role in modulation of SMC phenotype (as described above). In the invention, SMCs migrate from the media to the intima toward growth factor (especially PDGF) secreted after endothelial injury using laminin-binding α7 integrin. Because of the absence of fibronectin, SMCs can not switch their phenotype from a contractile to a synthetic phenotype. These cells can not proliferate to form a neointima. Furthermore, since fibronectin is known to facilitate SMC survival by providing integrin-mediated inhibition of apoptose, in absence of fibronectin, SMCs may enter apoptosis and disappear. The SMCs that migrate to the intima in the early stage of aneurysm formation are SMCs of contractile phenotype and expressed α1β1, α3β1, α7β1 and α8β1 integrins in contrast to SMCs in the neointima formation which are of synthetic phenotype and express α5β1 and αvβ3 integrins.

FIG. 1 illustrates an exemplary schema outlining embodiments of the present invention for cerebral aneurysm formation versus neointima formation. In certain embodiments of the invention, integrin α7β1 which is specific cell surface marker of SMCs (they are not expressed by endothelial cells nor platelets) and is characteristic of their contractile phenotype is the best antigenic subendothelial components in the arterial wall useful for in vivo immuno-detection of early-stage aneurysm. Data from the literature suggest a prominent role for β7 integrin in vascular remodeling as described above, and in specific embodiments β7 integrin is a useful target antigen.

In vivo, human medial contractile SMCs are surrounded by a basement membrane that contains laminin 1 and/or laminin 3 (Yao et al., 1997). Laminin 1 is not expressed by the basement membrane of endothelium (which is composed of laminin 8 and 10) (Halmann et al., 2005; Falk et al., 1999; Viranen et al., 2000). It has been demonstrated that α7 integrin binds to specific laminin isoforms mediating adhesion and migration of SMCs (Yao et al., 1996): α7 integrin binds to laminin 1 and a mixture of laminin 2 and 4 but not to laminin 5. In contrast, it has been demonstrated that Laminin 5, an ECM protein found predominantly in epithelial tissues is expressed at low-level in the intima of normal vessels but is overexpressed in the neointima of injured vessels (Kingsley et al., 2002). In specific aspects, laminin 1 is an antigenic subendothelial component of aneurismal lesions while laminin 5 is a marker of neointima formation.

In certain aspects of the invention, immunohistochemistry is utilized to characterize the in situ expression of α7 integrin and laminin-1 in the arterial wall of early aneurysmal lesions in an established animal model of cerebral aneurysm. In other aspects of the invention, the in vivo detection of cerebral aneurysms is characterized by nuclear imaging or molecular MRI using labeled antibodies directed against α7 integrin or laminin-1 injected intravascularly.

VI. Compounds of the Invention

The compounds of the invention (which may also be referred to as compositions of the invention) are prepared such that they are suitable for detection and/or therapy of an aneurysm in an individual. In general embodiments, the compounds comprise different combinations of a targeting molecule, a label, an intravascular targeting molecule, and a therapeutic agent.

A. Cell Targeting Molecule

The cell targeting molecule of the invention is any moiety that is suitable to target a composition to a smooth muscle cell at a cerebral aneurysm. In specific embodiments, the targeting molecule is an antibody or a peptide, and in particular cases the antibody or peptide targets proteins on the surface of the smooth muscle cell, such as proteins that are receptors, for example.

1. Antibodies

In specific embodiments of the invention, the cell targeting molecule is an antibody. Although the antibody may immunologically react with any target that identifies a smooth muscle cell at the site of an aneurysm, in specific embodiments the antibody targets a protein, such as a receptor, on the cell. In certain cases, the antibody will bind exclusively smooth muscle cells exposed at the luminal surface of the vessel, and in particular cases the antibody does not bind contractile smooth muscle cells in the medial layer of the normal arterial wall. In specific embodiment, the receptor is an integrin or is a laminin. In further specific embodiments, the antibody recognizes α7 integrin or laminin-1.

2. Peptides

In other embodiments of the invention, the cell targeting molecule is a peptide. Although the peptide may bind with any target on a smooth muscle cell at the site of an aneurysm, in specific embodiments the peptide targets a protein, such as a receptor, on the cell. In particular cases, the peptide will bind exclusively smooth muscle cells exposed at the luminal surface of the vessel, and in specific cases the peptide does not bind contractile smooth muscle cells in the medial layer of the normal arterial wall. In specific embodiment, the receptor is an integrin or is a laminin. In further specific embodiments, the peptide recognizes Δ7 integrin or laminin-1. In further specific embodiments, the peptide also known as peptidomimetic (small protein-like chain design to mimic a peptide) competes with laminin-1 to bind Δ7 integrin. This peptidomimetic of laminin-1 may be derived from the G domain of the α1 chain of laminin-1 such as the α1 chain amino acids 2179-2198 "SN peptide" (Khan et al., 2002)

B. Labels

In particular aspects of the invention, one or more labels are comprised on a composition of the invention. The label may be attached to the cell targeting molecule, the intravascular targeting molecule, and/or the therapeutic agent. Although any labels suitable in the art may be employed, in specific embodiments the label is a radionuclide, a fluorophore, a lucigen, or a paramagnetic chelator or microbubble contrast agent.

A label moiety may be attached to the antibody moiety using techniques readily available to the public. The label moiety may be a radioactive label such as a gamma ray emitting radionuclide: 111 Indium, Technetium-99m, iodine 123 (123I), iodine 125 (125I). A chelating agent such as dipropylaminetetraacetic acid (DPTA) may be used to associate the radioactive label to the antibody. The label moiety may be a positron emitting radionuclide such as Fluorin-18, carbon-11, Gallium 68. The label moiety may be a near infrared fluorophore (near infrared fluorescent dye) such as Cy7-NHS, Cy5.5 (Amersham Pharmacia). The label moiety may be a MRI contrast agent, such as paramagnetic lanthanide Gadolinium or superparamagnetic particles of iron oxide (SPIOs), for example. The label moiety may be also a microbubble contrast agent.

C. Intravascular Targeting Molecule

In general embodiments of the invention, the composition comprises a moiety that prevents the cell targeting molecule from moving beyond the luminal surface of the aneurysmal wall to bind smooth muscle cells in the medial layer of normal vascular wall that harbors an intact endothelium. Any macromolecular agent with intravascular retention may be coupled to the cell targeting molecule is useful. The molecule may have a molecular weight that confines it within the vessels, yet allows it to be cleared from the intravascular compartment. In a specific embodiment, the molecule is a macromolecule, and macromolecular species may include any molecule, natural or synthetic, which has a molecular weight in excess of 1 kilodalton such as but not limited to albumin, transferrin, globulins, pectin, gelatin, dextran, and cellulose derivatives, for example.

In specific embodiments, the molecule is a polymer. In particular embodiments, the molecule is dextran. Dextran is a hydrophilic molecule that does not pass the phospholipid bilayer of endothelial membrane. Antibody (or any cell targeting molecule) conjugated to dextran will not pass the endothelium. The conjugate will bind specifically smooth muscle cells at the luminal surface of the aneurysmal wall, such as α7 integrin or laminin-1 exposed at the luminal surface of the aneurysmal wall, and cannot bind α7 integrin or laminin-1 on SMCs in the medial layer of normal vascular wall that harbors an intact endothelium.

D. Therapeutic Agent

In particular aspects of the invention, the compounds for delivery to the individual with the aneurysm or suspected of having an aneurysm comprise one or more therapeutic agents. In specific cases, the therapeutic agent is bound directly to the label, the intravascular targeting molecule, and/or the cell targeting molecule. Although in specific cases the therapeutic agent comprises a thrombogenic or polymerisable molecule (intended to clog the aneurysms) or proteins (elastin, fibronectin, or fibrinogen, for example), or cell growth factors (intended to reinforce or make the fundus thicker and stronger).

Figure 2:
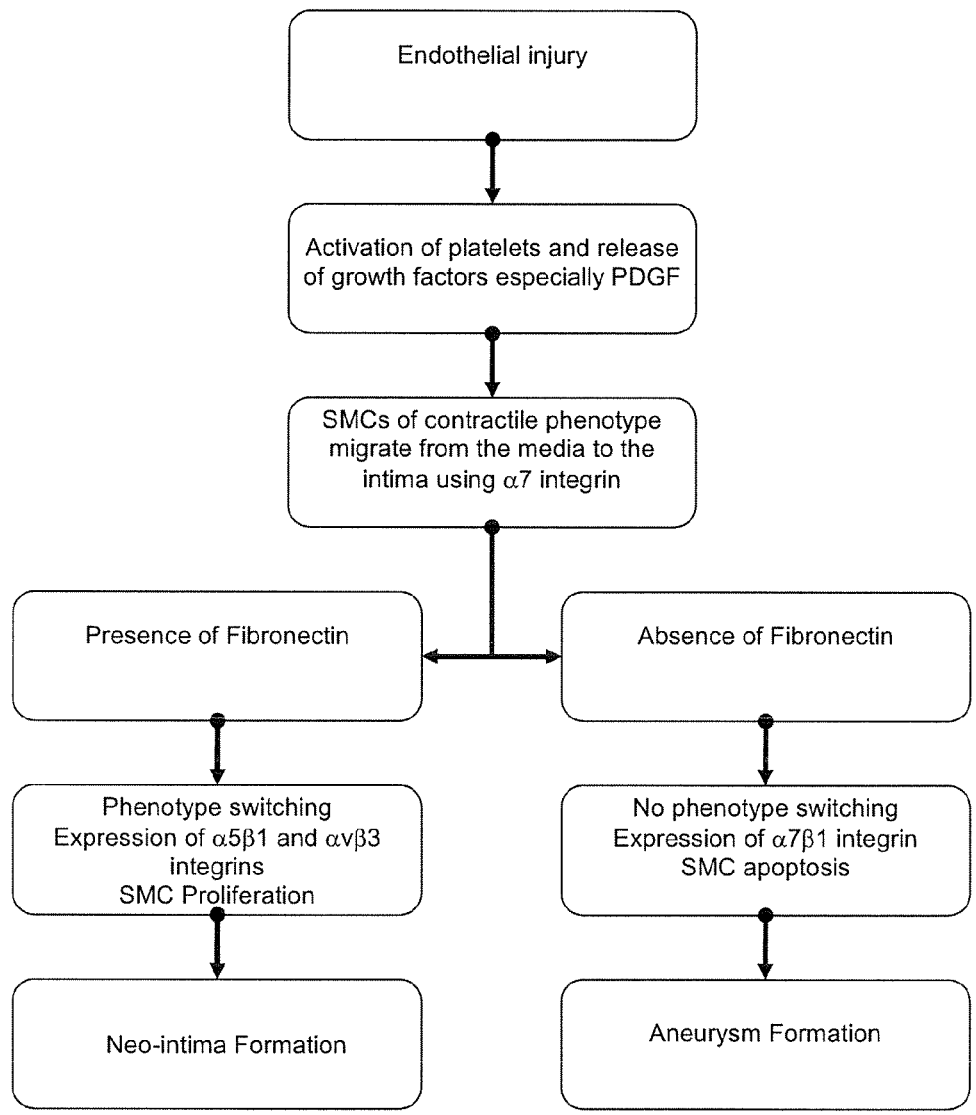
FIG. 2 is an exemplary schema outlining embodiments of the present invention regarding treatment of neo-intima formation vs. cerebral aneurysm.
Figure 2:
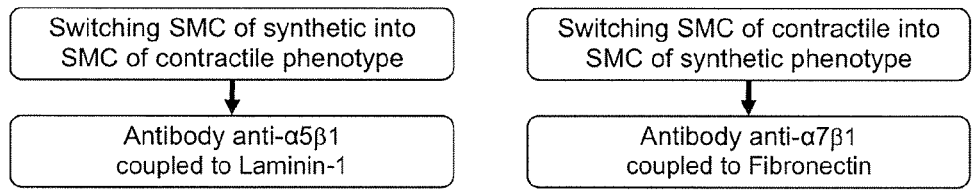

In a specific embodiment, the therapeutic agent is a compound able to convert SMCs of contractile phenotype into SMCs of synthetic phenotype. In a preferred embodiment, this compound comprises an antibody directed against α7β1 integrin coupled to fibronectin or fragments of fibronectin (specific fibronectin peptides). In an other embodiment, the anti-α7β1 integrin antibody is coupled to fibronectin or fragments of fibronectin (specific fibronectin peptides) and Growth Factors. In contrast to cerebral aneurysm formation, neo-intima formation that occurs in vascular disease such as re-stenosis after angioplasty, will be treated or prevented by using a compound able to convert SMCs of synthetic phenotype into SMCs of contractile phenotype. In this embodiment, the therapeutic agent is composed of antibody directed against α5β1 integrin coupled to laminin, and especially laminin-1. (FIG. 2).

E. Assembly of the Compounds

The compounds of the invention may be assembled in any suitable manner. In specific embodiments, however, Dextran is the molecule used as the intravascular targeting molecule. For nuclear imaging Technetium-99m-Dextran is prepared according to method known in the art (Line et al., 2000) and then coupled to the cell targeting molecule (antibody or peptide). 99mTc-Dextran is restricted to the blood pool and is broken down by the liver and cleared through the kidneys. These properties allow low background activity in the extra vascular space and rapid clearance from the intra vascular space. Radiolabeling through 99mTc-Dextran will avoid the diffusion of the compound to the extra vascular compartment. 99mTc-Dextran coupled to the cell targeting molecule will bind specifically SMCs of the luminal surface of the aneurysmal lesion and will not bind SMCs in the medial layer of normal artery. For molecular MRI, gadolinium-DPTA-Dextran will be prepared according to method known in the art (Sirlin C B et al., 2004) and coupled to the cell targeting molecule.

VII. Detection of the Compounds

Detection of a compound accumulated at the aneurysm site/or in the aneurysm vicinity may be performed according to techniques known in the art and which may vary depending on the characteristic of the label moiety of the conjugate. For example, when the conjugate comprises a gamma-ray emitting radionuclide, the aneurysm may be detected by scintigraphy using a gamma-camera or by single photon emission computed tomography (SPECT). When the conjugate comprises a positron emitting radionuclide, the aneurysm may be detected by positron emission tomography (PET). Combined positron emission tomography (PET) and computerized tomography (CT) or magnetic resonance (MR) can be used (PET/CT or PET/MR). This combined technique allows accurate detection and localization for aneurysmal lesions. When the conjugate comprises a MRI agent contrast, the aneurysm may be detected by MRI. When the conjugate comprises a positron emitting radionuclide, the aneurysm may be detected by positron emission tomography (PET). When the conjugate is a near infrared fluorophore (near infrared fluorescent dye), the aneurysm may be detected by near-infrared imager. When the conjugate is a microbubble contrast agent, the aneurysm may be detected by ultrasound imagery.

Thus, different molecular imaging techniques could be used depending on the nature of the labeling agent such as immunoscintigraphy and SPECT using antibody radiolabeled with 99mTc-dextran or MRI using antibody conjugated to Gadolinium-DTPA-dextran. Ultrasound may also be employed. Other techniques could use a positron emitting radionuclide and the aneurysm will be detected by positron emission tomography (PET).

VIII. Methods of Using the Compounds

In general embodiments of the invention, the compounds are employed to detect an aneurysm, and in further embodiments the compounds are used to treat an aneurysm. In certain cases the same compound is employed to detect the aneurysm as to treat the aneurysm, although in other cases a different compound is employed to detect the aneurysm as to treat the aneurysm. The methods may be employed in an individual suspected of having an aneurysm (symptomatic aneurysm, for example), an individual at risk for having an aneurysm (such as one with head trauma, high blood pressure, cigarette smoking, or having certain disease states known to be associated with an increased prevalence of aneurysm such as, but not limited to familial intracranial aneurysm, autosomal dominant polycystic kidney disease, fibrous dysplasia or coarctation of the aorta, for example), an individual that has a history of aneurysms, or an individual known to harbor aneurysm(s) (multiple aneurysms, for example).

A. Diagnosis

The present invention utilizes particular compounds to detect one or more aneurysms in an individual. In certain cases, the compound is delivered to the individual, the compound localizes to the aneurysm site, and the brain or a part thereof is monitored for detection of the compound. When the compound is detected at the localized site, the individual may be given therapy for the aneurysm, using a compound of the present invention having a therapeutic agent, endovascular coil embolization or surgical clip occlusion The detection of a signal at the major brain artery site and more particularly, at or near the apex of arterial forks may be indicative of a cerebral aneurysm. A positive detection of a signal may be followed by a digital subtraction angiography in patients in need thereof. Follow-up may be performed using the same method of diagnosis to ensure the disappearance or reduction of any intracranial labeling after treatment.

Currently, ruptured aneurysms are diagnosed with the aid of computerized tomography scanning followed by a 4-axle digital subtraction angiography.

Unruptured aneurysms are mainly found by serendipity during evaluation of neurological non-aneurysmal disease (incidental aneurysm), part of a multiple aneurysm constellation (multiple aneurysms), or those that are symptomatic (symptomatic aneurysm).

Both computerized tomography scanning and magnetic resonance angiography are poorer methods than digital subtraction angiography for detection of aneurysms smaller than 5 mm. Such invasive method cannot be used for mass detection.

Methods and compositions of the present invention that can non-invasively detect and treat ruptured as well as unruptured aneurysms is a more desirable embodiment and allows mass detection and preventive treatment.

B. Therapy

In particular aspects, the present invention employs a therapeutic agent on the compound, wherein the compound targets subendothelial components of an aneurysmal wall. In specific embodiments, the aneurysm is suspected of being in the individual, although in other cases the aneurysm has already been detected, including by a compound of the present invention, for example. The therapy may be delivered to the individual once or multiple times.

An exemplary embodiment of a therapeutic molecule may include for example, but not limited to a compound for inducing thrombosis, a compound for promoting aneurismal wall thickening and/or a compound for promoting cell growth. The therapeutic molecule may, more particularly be selected from the group consisting of a thrombogenic molecule, a polymerisable molecule (intended to clog the aneurysms), a protein (e.g., elastin, fibronectin, or fibrinogen etc), and a cell growth factor (intended to reinforce or make the fundus thicker and stronger). Another exemplary embodiment of a therapeutic molecule may include for example a protease inhibitor, such as an elastase inhibitor or a matrix metallo-proteinase inhibitor. Elastase inhibitors may include, without limitation, alpha-1 antitrypsin, alpha-2 macroglobulin which are the main elastase inhibitors in the serum. Elafin is also a potent inhibitor of elastase and proteinase 3 which is encompassed herewith. Matrix metallo-proteinase inhibitors may include, for example and without limitation tissue inhibitors of metallo-proteinase (T1 MPs) or synthetic inhibitors known in the art, such as tetracyclines and tetracycline derivatives such as doxycycline.

IX. Combination Therapy

In order to increase the effectiveness of a compound of the invention, it may be desirable to combine these compositions with other therapies effective in the treatment of aneurysms. More generally, these other compositions would be provided in a combined amount effective to treat the aneurysm. This process may involve treating the individual with the compound of the invention and the additional therapy (drugs and/or surgery and/or endovascular coiling) at the same time. In cases wherein the additional therapy is a compound, as opposed to surgery and/or endovascular coiling, this may be achieved by providing the individual with a single composition or pharmacological formulation that includes both agents, or by delivering to the individual with the two distinct compositions or formulations, at the same time, wherein one composition includes the therapy of the invention and the other includes the second agent(s).

In the context of the present invention, it is contemplated that the composition of the invention could be used in conjunction with surgery and/or endovascular coiling or drug(s). Alternatively, delivery of the compound of the present invention may precede or follow the other agent treatment by intervals ranging from minutes to weeks. In embodiments where the other agent (or surgery and/or endovascular coiling) and the compound of the present invention are delivered separately to the individual, one would generally ensure that a significant period of time did not expire between the time of each delivery, such that the other agent and compound of the invention would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

In some cases, the treatments are repeated as necessary.

X. Antibodies

In certain aspects of the invention, one or more antibodies are employed in the methods and compositions of the invention. These antibodies may be used in various diagnostic or therapeutic applications, described herein below. As used herein the term "antibody" means a polyclonal antibody, a monoclonal antibody, a chimeric antibody, a humanized antibody, a deimmunized antibody, an antigen-binding fragment, an Fab fragment; an F(ab')2 fragment, and Fv fragment, or a synthetic molecule comprising an antigen-binding fragment.

In some cases, the term "antibody" is intended to refer broadly to any immunologic binding agent such as IgG, IgM, IgA, IgD and IgE. In certain cases, IgG and/or IgM may be utilized, because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992) Biochem 31:1579-1584. The oligomerization domain comprises self-associating .alpha.-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) J Immunology 149B:120-126.

Antibody-like binding peptidomimetics are also contemplated in the present invention. Liu et al. Cell Mol Biol (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

A. Methods For Generating Monoclonal Antibodies

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756, 687, 5,750,172, and 5,741,957.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m2) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60 61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al., J Immunol Methods. 2002 Mar. 1; 261(1-2):1-20, for a discussion of myeloma expression systems.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Another embodiment of the invention for producing antibodies according to the present invention is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments encompassed by the present invention can be synthesized using an automated peptide synthesizer, or by expression of full-length gene or of gene fragments in E. coli.

B. Antibody Conjugates

The present invention further provides antibodies against contractile SMC surface proteins, polypeptides and peptides that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules that have been conjugated to antibodies include enzymes, radiolabels, radionuclides, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine211, 14carbon, 51chromium, 36chlorine, 57cobalt, 58cobalt, copper67, 152Eu, gallium67, 3hydrogen, iodine123, iodine125, iodine131, indium111, 59iron, 32phosphorus, rhenium186, rhenium188, 75selenium, 35sulphur, technicium99m and/or yttrium90. $^{125}$I is often being preferred for use in certain embodiments, and technicium99m and/or indium111 are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNC12, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6 α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment of the invention, the antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

XI. Pharmaceutical Preparations and Delivery

Pharmaceutical compositions of the present invention comprise an effective amount of one or more compositions of the invention or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one composition of the invention or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The composition of the invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The present invention is generally intravascularly (intra-arterially or intravenously) administered, or may be delivered in situ via an arterial catheter. The administration can be injection, infusion, or continuous infusion.

In some embodiments of the invention, systemic injection is employed for delivery, whereas in other embodiments of the invention there is local or in situ administration using a catheter (same technique as coiling, for example) in order to increase the local concentration of the antibody while decreasing the blood concentration in the systemic bloodstream/circulation.

In an other embodiment, a coil coated with the therapeutic compound is brought to the aneurysm via an arterial catheter using a standardized endovascular coiling technique.

This coil behaves as a drug delivery system and therefore realizes an in situ continuous infusion of the composition.

Once released within the aneurysm, the coated coil deploys blocking or decreasing the blood flow into the aneurysm. These conditions allow the topical delivery of the therapeutic agent and promote its assimilation within the aneurysmal wall.

This dual mechanism combines a short-term effect of clogging the aneurysmal lumen and the long-term effect of repairing the aneurysmal wall.

Both combined actions are aimed to preclude a new hemorrhage when a re-permeabilization occurs after coiling. The simultaneous delivery of the therapeutic agent to the aneurysm will repair the aneurysmal wall and prevent any hemorrhagic recurrence.

The composition of the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include composition of the invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the composition of the invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, composition of the invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

XII. Kits

Any of the compositions described herein may be comprised in a kit for the detection and/or treatment of aneurysm. The kit may include a cell targeting molecule, a label, an intravascular targeting molecule, and/or a therapeutic agent. These components may or may not be assembled into one composition. In a non-limiting example, there may be an additional agent provided in the kit. The kits may thus comprise, in suitable container means, a composition of the invention and, optionally, an additional agent of the present invention. Kits of the present invention will generally contain, in suitable container means, a pharmaceutically acceptable formulation of the composition of the invention.

The component(s) of the kits may be packaged either in aqueous media or in lyophilized form. When reagents and/or components are provided as a dry powder, the powder can be reconstituted by the addition of a suitable solvent. It is envisioned that the solvent may also be provided in another container means. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition of the invention and any other reagent containers in close confinement for commercial sale. Such containers may include injection or blow molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Experimental Designs and Methods

The present example provides exemplary materials and methods for the invention, although one of skill in the art recognizes that they are merely exemplary in nature and may be modified within routine standards in the art.

1. In Situ Immunohistochemistry
Animal Preparation

Intracranial aneurysms are induced in 20 male Sprague-Dawley rats (age range, 6 to 7 weeks) according to the method of Hashimoto et al (Hashimoto et al., 1978). Ligation of the left common carotid artery and the posterior branches of both renal arteries will be performed under anesthesia with the use of an intraperitoneal injection of chloral hydrate (3%, 0.01 mL/g body wt). One week after the operation, 1% saline will be substituted for drinking water. The previous literature reported this method of preferentially induced experimental cerebral aneurysms at the right anterior cerebral artery (ACA)-olfactory artery (OA) bifurcations, where hemodynamic stress is assumed to increase by the ligation of the opposite common carotid artery (Kojima et al., 1986). An additional 5 age-matched rats will served as controls.

Three months after the aneurysm induction procedure, the rats will be cannulated into the ascending aorta through the left cardiac ventricle under general anesthesia and perfused at a pressure of 80 mmHg with 4% paraformaldehyde in PBS. After the perfusion fixations, the major arteries at the base of the brain will be carefully dissected under a surgical microscope. The specimens will be further immersed in 4% paraformaldehyde in PBS for 24 hours. The specimens will be rinsed with PBS, embedded in OCT compound (Tissue-Tek, Inc) and 7 µm-thick serial sections from ACA/OlfA bifurcation will be cut with a cryotome.
Light Microscopic Examination Using elastica-van Gieson stain and a light microscope, we will examine the bifurcation of the ACA and OA on both sides and examine aneurismal changes on the nonligated side.
Definition of Aneurysmal Changes It is established that fragmentation and disappearance of internal elastic lamina is a characteristic histological feature of aneurysmal lesions. Therefore, aneurysmal changes will be defined as lesions representing the outward dilatation of the wall that are accompanied by discontinuity of the internal elastic lamina in more than half the length of the dilated wall (evidenced by elastica-van Gieson staining). The lesions will be classified into two stages: (1) a stage of early aneurismal lesion preserving the smooth cell layer in the whole area of the wall and (2): saccular aneurysm lacking the smooth muscle layer even in part of the whole area of the lesion. Moreover, to detect endothelial injury at the apical intimal pad which is characteristic of early aneurismal lesion, we will performed immunohistochemical study using antibody against eNOS (endothelial injury is evidenced by the loss of eNOS expression).

Immunohistochemical Studies

Immunohistochemical studies will be performed on early aneurismal lesions and saccular aneurysm to study α7 integrin and laminin-1 expression. Our goal is to demonstrate that early aneurismal lesions show a lack of eNOS expression and a subendothelial staining for α7 integrin and laminin-1 in contrast to control sections that show a positive expression of eNOS and a medial without subendothelial staining for α7 integrin and laminin-1. Sections will be fixed in ice-cold acetone (10 minutes), air-dried (30 minutes), and incubated in 5% skim milk (30 minutes) before overnight incubation at 4° C. with primary antibodies. The primary antibodies will be mouse anti-eNOS antibody (BD Biosciences), mouse anti-rat α7 integrin antibody (H36 provide by S J Kaufman) rabbit polyclonal anti-laminin α-1 (H-300) (sc-5582, Santa Cruz Biotechnology, Inc). Sections will be washed with PBS, then incubated 30 minutes with fluorescein-conjugated secondary antibody (Alexa Fluor 594, 488 and 647 goat anti-mouse, anti-rabbit or anti-rat immunoglobulin G; Molecular Probes). For double immunofluorescence staining (eNOS and α7, eNOs and laminin-1) the same procedure will be repeated. After washing with PBS, the specimens will be mounted with Vectashield (Vector Laboratories).

Slides will be inspected under a fluorescent microscope combined with a laser confocal system. Image files will be digitally processed using Adobe Photoshop (Adobe Systems).

2. In Vivo Immunodetection of Aneurysmal Lesions

Molecular Imaging techniques well suitable for intravascular applications will be used such as immunoscintigraphy using antibody radiolabeled with 99mTc-dextran and/or MRI using antibody conjugated to Gadolinium-DTPA-dextran.

Dextran is a hydrophilic molecule that does not pass the phospholipid bilayer of endothelial membrane. Antibody conjugated to dextran will not pass the endothelium. The conjugate will bind specifically α7 integrin or laminin-1 exposed at the luminal surface of the aneurysmal wall and can not bind α7 integrin or laminin-1 on SMCs in the medial layer of normal vascular wall that harbors an intact endothelium. Dextran is useful in the invention, but any macromolecular agent with intravascular retention may be coupled to the antibody.

REFERENCES

The following references, to the extent that they provide exemplary procedural or other details supplementary to those set forth herein, are specifically incorporated herein by reference.

Patents and Patent Applications

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,741,957
U.S. Pat. No. 5,750,172
U.S. Pat. No. 5,756,687
U.S. Pat. No. 5,827,690
U.S. Pat. No. 6,091,001

PUBLICATIONS

Agnoli A L. Vascular anomalies and subarachnoid haemorrhage associated with persisting embryonic vessels. Acta Neuropathol (Wien) 1982 (60):183-199

Bauters C, Marotte F, Hamon M, et al. Accumulation of fetal fibronectin mRNAs after balloon denudation of rabbit arteries. Circulation 1995; 92:904-911.

Belkin V M, Belkin A M and Koteliansky V E. Human smooth muscle VLA-1 integrin: purification, substrate specificity, localization in aorta, and expression during development. J Cell Biol 1990; November 111:2159-2170

Boudreau N, turley E, Rabinovitch M. Fibronectin, hyaluronan, and a hyaluronan binding protein contribute to increased ductus arteriosus smooth muscle cell migration. Dev Biol 1991; 143:235-247.

Bremer J L. Congenital aneurysms of the cerebral arteries. Arch Pathol 1943 (35): 819-831

Broderick J P, Brott T G, Duldner J E et al. Initial and recurrent bleeding are the major causes of death following subarachnoid hemorrhage. Stroke 1994; 25: 1342-1347.

Cajander S, Hassler O. Enzymatic destruction of the elastic lamella at the mouth of cerebral berry aneurysm? An ultrastructural study with special regard to the elastic tissue. Acta Neurol Scand. 1976 March; 53(3):171-81

Campbell G R, Campbell G H. Smooth muscle phenotypic changes in arterial wall homeostasis: implications for the pathogenesis of atherosclerosis. Exp Mol Pathol. 1985; 42:139-162

Chemnitz J, Collatz Christensen B. Repair in arterial tissue: demonstration of fibronectin in the normal and healing rabbit thoracic aorta by the indirect immunoperoxidase technique. Virchows Arch A Pathol Anat Histopathol. 1983; 399:307-316.

Cheuk B L, Cheng S W. Differential expression of integrin a5b1 in human abdominal aortic aneurysm and healthy aortic tissues and its significance in pathogenesis. J Surg Res 2004 May 15; 118(2):176-182.

Clyman R I, Tannenbaum J, Chen Y Q, et al. Ductus arteriosus smooth muscle cell migration on collagen: dependence on laminin and its receptors. J Cell Science 1994; 107:1007-1018.

Cohen J R, Parikh S, Grella L et al. Neutrophil elastase mRNA transcripts in abdominal aortic aneurysm patients. Surgical forum 1991(42):358-359

Echtermeyer F, Schober S, Poschl E et al. Specific induction of cell motility on laminin by a7 integrin. J Biol Chem 1996; 271:2071-2075.

Falk M, Ferletta M, Forsberg E et al. Restricted distribution of laminin alpha 1 chain in normal adult mouse tissues. Matrix Biol 1999 December; 18(6): 557-568

Forbus W D: On the origin of military aneurysms of the superficial cerebral arteries. Bull Johns Hopkins Hosp 1930, 47:239-284

Fukuda S, Hashimoto N, Naritomi H, Nagata I, Nozaki K, Kondo S, Kurino M, Kikuchi H. Prevention of rat cerebral aneurysm formation by inhibition of nitric oxide synthase. Circulation 2000(101):2532-2538

Futami K, Yamashita J, Tachibana O et al. Immunohistochemical alterations of fibronectin during formation and proliferative repair of experimental cerebral aneurysms in rats. Stroke 1995; 26: 1659-1664.

Glukhova M, Koteliansky V, Fondacci C et al. Laminin variants and integrin laminin receptors in developing and adult human smooth muscle. Dev Biol 1993; 157: 437-447.

Glynn L E: Medial defects in the circle of Willis and their relation to aneurysm formation. J Pathol Bacteriol 1940 (51): 213-222

Gotwals P J, Chi-Rosso G, Lindner V et al. The a1b1 integrin is expressed during neointima formation in rat arteries and mediates collagen matrix reorganization. J Clin Invest 1996; 97:2469-2477

Greenhill N S, Stehbens W E. Scanning electron-microscopic study of the inner surface of experimental aneurysms in rabbits. Atherosclerosis 1982 December 45(3):319-30

Hackett M L, Anderson C. Health outcomes 1 year after subarachnoid hemorrhage: an international population-based study. The Australian Cooperative Research on Subarachnoid Hemorrhage Study group. Neurology 2000; 55: 658-662.

Hallmann R, Horn N, Selg M et al. Expression and function of laminins in the embryonic and mature vasculature. Physiol Rev 2005; 85: 979-1000.

Hashimoto N, Handa H, Hazama F. Experimentally induced aneurysms in rat. Surg Neurol 1978; 10: 3-8.

Hazama F, Kataoka H, Yamada E, Kayembe K, Hashimoto N, Kojima M, Kim C. Early changes of experimentally induced cerebral aneurysms in rats. Light-microscopic study. Am J Pathol. 1986 September; 124(3):399-404

Hedin U, Johan T. Plasma fibronectin promotes modulation of arterial smooth-muscle cells from contractile to synthetic phenotype. Differentiation 1987; 33:239-246.

Hillis G S, Mlynski R A, Simpson J G et al. The expression of beta 1 integrins in human coronary artery. Basic Res Cardiol 1998 August; 93:295-302.

Hoshiga M, Alpers C E, Smith L L. avb3 integrin expression in normal and atherosclerotic artery. Cir Res 1995; 77:1129-1135.

Houghton A M, Quintero P A, Perkins D L, Kobayashi D K, Kelley D G, Marconcini L A, Mecham R P, Senior R M, Shapiro S D. Elastin fragments drive disease progression in a murine model of emphysema. The Journal of Clinical Investigation 2006(116):753-759.

Hultgardh-Nilsson A, Lovdahl C, Blomgren K, et al. Expression of phenotype- and proliferation-related genes in rat aortic smooth muscle cells in primary culture. Cardiovasc Res 1997 May; 34(2):418-30

Iwamoto H, Kiyohara Y, Fujishima M et al. Prevalence of intracranial saccular aneurysms in a Japanese community based on a consecutive autopsy series during a 30-year observation period. The Hisayama study. Stroke 1999; 30: 1390-1395.

Jamous M A, Nagahiro S, Kitazato K T et al. Endothelial injury and inflammatory response induced by hemodynamic changes preceding intracranial aneurysm formation: experimental study in rats. J Neurosurg 2007; 107: 405-411.

Juvela S: [Alcohol and the prognosis of subarachnoid hemorrhage.] Duodecim 109:355-357, 1993 (Fin)

Juvela S: Natural history of unruptured intracranial aneurysms: risks for aneurysm formation, growth, and rupture. Acta Neurochir Suppl 82:27-30, 2002

Juvela S, Porras M, Poussa K: Natural history of unruptured intracranial aneurysms: probability of and risk factors for aneurysm rupture. J Neurosurg 93:379-387, 2000

Juvela S, Poussa K, Porras M: Factors affecting formation and growth of intracranial aneurysms: a long-term follow-up study. Stroke 32:485-491, 2001

Khan F, Laurie G W, McCaffrey T A et al. Exposure of cryptic domains of the □1 chain of laminin-1 by elastase stimulates macrophages urokinase and matrix metalloproteinase-9 expression. J Biol Chem 2002; 277:13778-13786.

Kim C, Cervos-Navarro J, Kikuchi H, Hashimoto N, Hazama F. Alterations in cerebral vessels in experimental animals and their possible relationship to the development of aneurysms Surg Neurol 1992 November; 38(5):331-337

Kim C, Kikuchi H, Hashimoto N, Kojima M, Kang Y, Hazama F. Involvement of Internal Elastic Lamina in Development of Induced Cerebral Aneurysms in Rats. Stroke 1988; 19:507-511

Kingsley K, Huff J L, Rust W L. ERK1/2 mediates PDGF-BB stimulated vascular smooth muscle cell proliferation and migration on laminin-5. Biochem Biophys Res Commun 2002 May 10; 293:1000-1006.

Kojima M, Handa H, Hashimoto N, Kim C, Hazama F. Early changes of experimentally induced cerebral aneurysms in rats: scanning electron microscopic study. Stroke 1988; 19:507-11.

Kojima M, Handa H, Hashimoto N, Kim C, Hazama F. Early changes of experimentally induced cerebral aneurysms in rats: scanning electron microscopic study. Stroke 1986; 17:835-41.

Kondo S, Hashimoto N, Kikuchi H, Hazama F, Nagata I, Kataoka H. Apoptosis of Medial Smooth Muscle cells in the development of Saccular Cerebral Aneurysms in rats. Stroke 1998(29):181-189.

Line B R, Weber P B, et Lukasiewicz R et al. Reduction of background activity through radiolabeling of antifebrin Fab' with 99mTc-Dextran. J nucl med 2000, 41:1264-1270.

Molossi S, Elices M, Arrhenius T, et al. Lymphocyte transendothelial migration toward smooth muscle cells in interleukin-1b-stimulated co-cultures is related to fibronectin interactions with a4b1 and a5b1 integrins. J Cell Physiol 1995; 164:620-633.

Molyneux A J, Kerr R S C, Yu L M, et al. International subarachnoid aneurysm trial (ISAT) of neurosurgical clipping versus endovascular coiling in 2143 patients with ruptured intracranial aneurysms: a randomized trial. The Lancet 360: 1267-1274, 2002.

Morimoto M, Miyamoto S, Mizoguchi A, Kume N, Kita T, Hashimoto N. Mouse model of cerebral aneurysm: experimental induction by renal hypertension and local hemodynamic changes. Stroke. 2002 July; 33(7):1911-5

Nagata I, Handa H, Hasimoto N, Hazama F. Experimentally induced cerebral aneurysms in rats: VII. Scanning electron microscope study. Surg Neurol. 1981 October; 16(4):291-6

Nakatani H, Hashimoto N, Kang Y, Yamazoe N, Kikuchi H, Yamaguchi S, Niimi H. Cerebral blood flow patterns at major vessel bifurcations and aneurysms in rats. J Neurosurg 1991; (74):258-262

Pickering J G, Chow L H, Li S et al. a5b1 integrin expression and luminal edge fibronectin matrix assembly by smooth muscle cells after arterial injury. Am J Pathol 2000; 156: 453-465.

Raaymakers T W, Rinkel G J, Ramos L M: Initial and follow-up screening for aneurysms in families with familial subarachnoid hemorrhage. Neurology 51:1125-1130, 1998

Remington's Pharmaceutical Sciences, 18th Ed. Mack Printing Company, 1990.

Ronkainen A, Hernesniemi J, Puranen M, et al: Familial intracranial aneurysms. Lancet 349:380-384, 1997

Schnapp L M, Breuss J M, Ramos D M et al. Sequence and tissue distribution of the human integrin a8 subunit: a b1-associated a subunit expressed in smooth muscles cells. J Cell Scie 1995; 108:537-544.

Schwartz S M, Reidy M A. Common mechanisms of proliferation of smooth muscle in atherosclerosis and hypertension. Hum Pathol 1987; 18:240-247

Sekhar L N, Heros R C. Origin, growth and rupture of saccular aneurysms: A review. Neurosurgery 1981 (8): 248-260

Sirlin C B, Vera D R, Corbeil J A et al. Gadolinium-DTPA-Dextran: A macromolecular MR blood pool contrast agent. Academic Radiology 2004; 11:1361-1369

Sjolund M, Hedin U, Sejersen T, et al. Arterial smooth muscle cells express platelet-derived growth factor (PDGF) A chain mRNA, secrete a PDGF-like mitogen, and bind exogenous PDGF in a phenotype- and grow state-dependent manner. J Cell Biol 1988; 106:403-413.

Stehbens W E. Etiology of intracranial berry aneurysms. J Neurosurg 1989 (70):823-831

Stehbens W E. Histopathology of cerebral aneurysms. Arch Neurol 1963 (8):272-285

Stehbens W E: Intracranial arterial aneurysms, In: Stehbens W E. Pathology of the Cerebral Blood Vessels. Edited by W E Stehbens. St Louis, C V. Mosby, 1972, pp 351-470

The International Study of Unruptured Intracranial Aneurysms Investigators: Unruptured intracranial aneurysms—risk of rupture and risks of surgical intervention. N Engl J Med 339:1725-1733, 1998

Thorsteinsdottir S, Roelen B A, Freund E et al. Expression patterns of laminin receptor splice variants alpha6Abeta1 and alpha6Bbeta1 suggest different roles in mouse development. Dev Dynam 1995; 204:240-258.

Thyberg J, Blomgren K, Roy J, et al. Phenotypic modulation of smooth muscle cells after arterial injury is associated with changes in the distribution of laminin and fibronectin. J Histochem Cytochem 1997; 45:837-846.

Thyberg J. Differentiated properties and proliferation of arterial smooth muscle cells in culture. Int Rev Cytol 1996; 169:183-265

Topol E J, Ferguson J J, Weisman H F et al. Long-term protection from myocardial ischemic events in a randomized trial of brief integrin b3 blockade with percutaneous coronary intervention. JAMA 1997; 278:479-484.

Virtanen I, Gullberg D, Rissanen J et al. Laminin alpha 1-chain shows a restricted distribution in epithelial basement membranes of fetal and adult human tissues. Exp Cell Res 2000 Jun. 15; 257 (2): 298-309.

Welser J V, Lange N, Singer C A. Loss of the $\alpha 7$ integrin promotes extracellular signal-regulated kinase activation and altered vascular remodeling. Circ Res 2007; 101: 672-681.

Yamada E, Hazama F, Kataoka H, Amano S, Sasahara M, Kayembe K, Katayama K: Elastase-like enzyme in the aorta of spontaneously hypertensive rats. Virchows Arch [Cell Pathol] 1983, 44:241-245

Yao C C, Breuss J, Pytela R et al. Functional expression of the alpha 7 integrin receptor in differentiated smooth muscle cells. J Cell Science 1997; 110:1477-1487.

Yao C C, Ziober B L, Squillace M et al. $\alpha 7$ integrin mediates cell adhesion and migration on specific laminin isoforms J Biol Chem 1996; 271(41): 25598-25603.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of detecting a cerebral aneurysm in an individual, comprising the steps of a) delivering an effective amount to the individual of a composition comprising a labeled antibody that specifically binds to $\alpha 7$ integrin expressed on contractile smooth muscle cells (SMCs) present in the intima of a cerebral aneurysm, wherein the labeled antibody localizes to the cerebral aneurysm site, and a pharmaceutically acceptable excipient, and b) monitoring the individual's brain for detection of the labeled antibody, wherein detection of the labeled antibody at a brain artery site is indicative of a cerebral aneurysm in the individual.

2. The method of claim 1, wherein the individual has risk factors for harboring an aneurysm.

3. The method of claim 1, wherein the individual has a family history of aneurysm.

4. The method of claim 1, wherein the individual is asymptomatic with no history or known risk of cerebral aneurysm.

5. The method of claim 1, wherein the composition is delivered to the individual once.

6. The method of claim 1, wherein the composition is delivered to the individual more than once.

7. The method of claim 1, wherein the composition is delivered intravascularly.

8. The method of claim 1, wherein the composition is delivered in situ via an arterial catheter.

9. A method of identifying an individual having a cerebral aneurysm prone to rupture, comprising the steps of a) delivering to the individual known to have or suspected of having a cerebral aneurysm an effective amount of a composition comprising a labeled antibody that specifically binds to $\alpha 7$ integrin expressed on contractile SMCs present in the intima of a cerebral aneurysm, wherein the labeled antibody localizes to the cerebral aneurysm site, and a pharmaceutically acceptable excipient, to the individual known to have or suspected of having a cerebral aneurysm, and b) monitoring the individual's brain for detection of the labeled antibody, wherein detection of the labeled antibody at a brain artery site is indicative of a cerebral aneurysm prone to rupture in the individual.

10. The method of claim 1, further comprising determining a risk of the cerebral aneurysm rupturing, comprising determining a ratio of expression of $\alpha 7\beta 1$ integrin to expression of $\alpha 5\beta 1$ integrin, wherein an elevated ratio of $\alpha 7\beta 1$ integrin expression to expression of $\alpha 5\beta 1$ integrin indicates a risk of the cerebral aneurysm rupturing.

11. The method of claim 9, further comprising determining a risk of the cerebral aneurysm rupturing, comprising determining a ratio of expression of $\alpha 7\beta 1$ integrin to expression of $\alpha 5\beta 1$ integrin, wherein an elevated ratio of $\alpha 7\beta 1$ integrin expression to expression of $\alpha 5\beta 1$ integrin identifies an individual having a cerebral aneurysm prone to rupture.

12. The method of claim 1, wherein the labeled antibody is conjugated to an intravascular targeting molecule.

13. The method of claim 12, wherein the intravascular targeting molecule is a polymer.

14. The method of claim 13, wherein the polymer is one selected from the group consisting of: dextran, albumin, transferrin, globulins, pectin, gelatin, and cellulose derivatives.

* * * * *